(12) United States Patent
Schoenafinger et al.

(10) Patent No.: US 7,094,800 B2
(45) Date of Patent: Aug. 22, 2006

(54) CYANOPYRROLIDIDES, PROCESS FOR THEIR PREPARATION AND THEIR USE AS MEDICAMENTS

(75) Inventors: Karl Schoenafinger, Alzenau (DE); Holger Wagner, Schwalbach/Ts. (DE); Gerhard Jaehne, Frankfurt (DE); Holger Gaul, Runkel (DE); Christian Buning, Bonn (DE); Georg Tschank, Essenheim (DE); Ulrich Werner, Miehlen (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 43 days.

(21) Appl. No.: 10/898,752

(22) Filed: Jul. 26, 2004

(65) Prior Publication Data

US 2005/0059724 A1 Mar. 17, 2005

Related U.S. Application Data

(60) Provisional application No. 60/527,697, filed on Dec. 8, 2003.

(30) Foreign Application Priority Data

Jul. 25, 2003 (DE) .................. 103 33 935
Apr. 21, 2004 (DE) .................. 10 2004 019 276

(51) Int. Cl.
*A61K 31/40* (2006.01)
*A61K 31/4439* (2006.01)
*C07D 209/02* (2006.01)
*C07D 401/02* (2006.01)

(52) U.S. Cl. ............. 514/413; 548/512; 548/466; 548/467; 546/276.7; 546/200; 514/323; 514/339

(58) Field of Classification Search ......... 548/512, 548/466; 514/413; 546/267.7, 200
See application file for complete search history.

(56) References Cited

U.S. PATENT DOCUMENTS

| | | | |
|---|---|---|---|
| 6,221,633 | B1 | 4/2001 | Ertl et al. |
| 6,221,897 | B1 | 4/2001 | Frick et al. |
| 6,245,744 | B1 | 6/2001 | Frick et al. |
| 6,342,512 | B1 | 1/2002 | Kirsch et al. |
| 6,380,357 | B1 | 4/2002 | Hermeling et al. |
| 6,624,185 | B1 | 9/2003 | Glombik et al. |
| 6,884,812 | B1 | 4/2005 | Glombik et al. |

FOREIGN PATENT DOCUMENTS

| | | |
|---|---|---|
| DE | 10142734 | 3/2003 |
| EP | 0485219 | 5/1992 |
| EP | 0462884 | 6/1993 |
| WO | WO 91/11457 | 8/1991 |
| WO | WO 97/26265 | 7/1997 |
| WO | WO 97/41097 | 11/1997 |
| WO | WO 99/03861 | 1/1999 |
| WO | WO 99/15525 | 4/1999 |
| WO | WO 99/31507 | 6/1999 |
| WO | WO 00/34331 | 6/2000 |
| WO | WO 00/34332 | 6/2000 |
| WO | WO 00/40569 | 7/2000 |
| WO | WO 00/63208 | 10/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 | 12/2000 |
| WO | WO 01/04156 | 1/2001 |
| WO | WO 01/09111 | 2/2001 |
| WO | WO 01/83451 | 11/2001 |
| WO | WO 01/85695 | 11/2001 |
| WO | WO 01/91752 | 12/2001 |

OTHER PUBLICATIONS

Boyd et al, "y-Lactam Analogues of Carbapenems," Tetrahedron Letters, vol. 27, No. 30, pp. 3457-3460 (1986).*
Aicher, et al., Substituted Tetrahydroprrolo[2,1-b]Oxazol-5(6H)-Ones and Tetrahydropyrrolo[2,1-b]Thiazol-5(6H)-Ones as Hypoglycemic Agents1, J. Med. Chem. (1998) vol. 41, pp. 4556-4566.
Asakawa, A., et al., Cocaine-Amphetamine-Regulated Transcript Infuences Energy Metabolism, Anxiety and Gastric Emptying in Mice, Hormone and Metabolic Research, 2001, vol. 33(9), pp. 554-558.
Lee Daniel W et al., Leptin agonists as a potential approach to the treatment of obestiy, Drugs of the Future, 2001, vol. 26(9), pp. 673-881.
Okada Hiroshi et al., Synthesis and Antitumor Activities of Prodrugs of Benzoylphemylureas, Chem. Pharm. Bull., 1994, vol. 42(1), pp. 57-61.

(Continued)

*Primary Examiner*—Taofiq Solola
*Assistant Examiner*—Andrew B. Freistein
(74) *Attorney, Agent, or Firm*—Barbara E. Kurys

(57) ABSTRACT

The invention relates to compounds of the formula I

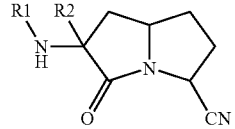

Formula I in which the radicals have the meanings stated in the text, their stereoisomeric forms, and their physiologically tolerated salts, physiologically functional derivatives and process for their preparation.

The compounds are suitable for the treatment of disorders of metabolism, such as type 2 diabetes.

10 Claims, No Drawings

OTHER PUBLICATIONS

Salvador Javier et al., Perspectives in the therapeutic use of leptin, Expert Opinion Pharmacotherapy 2001, 2(10), 1615-1622.

Tyle, Praveen, Iontophoretic Devices for Drug Delivery, Phamaceutical Research, vol. 3, No. 6, 1986 pp. 318-326.

Zunft, H. et al., Carob Pulp Preparation for Treatment of Hypercholesterolemia, Advances in Therapy, 2001, vol. 18(5), pp. 230-236.

* cited by examiner

CYANOPYRROLIDIDES, PROCESS FOR THEIR PREPARATION AND THEIR USE AS MEDICAMENTS

The invention relates to substituted cyanopyrrolidides and to their physiologically tolerated salts.

Compounds of similar structure and their use in a screening have already been described in the prior art (WO 99/31507).

The invention was based on the object of providing compounds which display a therapeutically utilizable blood glucose-lowering effect and are suitable in particular for the treatment of diabetes.

The invention therefore relates to compounds of the formula I,

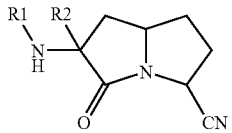

wherein

R1 is H, $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, heterocyclyl, COR3, COOR3, CONR3R4, CN, wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, SH, $SF_5$, OH, $(C_1-C_6)$-alkyl, $-CF_3$, $(C_2-C_6)$-alkenyl, $(C_2-C_6)$-alkynyl, OR3, $OP(O)(OR3)_2$, NR3R4, NR3CONR3R4, COR3, OCOR3, OCOOR3, COOR3, CONR3R4, OCONR3R4, $(C_1-C_6)$-alkylene-OR3, $(C_1-C_6)$-alkylene-NR3R4, $(C_1-C_6)$-alkylene-NR3SO₂R4, $(C_1-C_6)$-alkylene-SR3, alkylene-S(O)R3, alkylene-S(O)₂R3, alkylene-S(O)₂NR3R4, $(C_1-C_6)$-alkylene-COR3, $(C_1-C_6)$-alkylene-COOR3, $(C_1-C_6)$-alkylene-CONR3R4, SR3, SOR3, SO₂R3, SO₂NR3R4, NR3SO₂R4, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl;

R2 is H, $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, heterocyclyl, COR3, COOR3, CONR3R4 or CN, wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, SH, $SF_5$, OH, $(C_1-C_6)$-alkyl, $-CF_3$, $(C_2-C_6)$-alkenyl, $(C_2-C_6)$-alkynyl, OR3, $OP(O)(OR3)_2$, NR3R4, NR3CONR3R4, COR3, OCOR3, OCOOR3, COOR3, CONR3R4, OCONR3R4, $(C_1-C_6)$-alkylene-OR3, $(C_1-C_6)$-alkylene-NR3R4, $(C_1-C_6)$-alkylene-NR3SO₂R4, $(C_1-C_6)$-alkylene-SR3, alkylene-S(O)R3, alkylene-S(O)₂R3, alkylene-S(O)₂NR3R4, $(C_1-C_6)$-alkylene-COR3, $(C_1-C_6)$-alkylene-COOR3, $(C_1-C_6)$-alkylene-CONR3R4, SR3, SOR3, SO₂R3, SO₂NR3R4, NR3SO₂R4, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl;

R3, R4 are each, independently of one another, H, $(C_1-C_6)$-alkyl, $-CF_3$, $(C_3-C_{10})$-cycloalkyl, $(C_6-C_{10})$-aryl, heterocyclyl, $(C_1-C_6)$-alkylene-CONR5R6, CONR5R6, $(C_1-C_6)$-alkylene-COOR5, COOR5, COR5, $(C_1-C_6)$-alkylene-COR5, $(C_1-C_6)$-alkylene-OR5, $(C_1-C_6)$-alkylene-NR5R6, $(C_1-C_6)$-alkylene-SR5, $(C_1-C_6)$-alkylene-S(O)R5, $(C_1-C_6)$-alkylene-S(O)₂R5, S(O)R5, S(O)₂R5, $(C_1-C_4)$-alkylene-$(C_6-C_{10})$-aryl, or $(C_1-C_4)$-alkylene-heterocyclyl;

R5, R6 are each, independently of one another, H, $(C_1-C_6)$-alkyl, $(C_1-C_6)$-alkylene-$(C_6-C_{10})$-aryl, $-(C_6-C_{10})$-aryl, heterocyclyl or $(C_1-C_6)$-alkylene-heterocyclyl;

and pharmaceutically acceptable salts thereof.

Preference is given to compounds of the formula I in which one or more radicals mean R1 is H;

R2 is H, $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, heterocyclyl, COR3, COOR3, CONR3R4 or CN, wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, SH, $SF_5$, OH, $(C_1-C_6)$-alkyl, $-CF_3$, $(C_2-C_6)$-alkenyl, $(C_2-C_6)$-alkynyl, OR3, $OP(O)(OR3)_2$, NR3R4, NR3CONR3R4, COR3, OCOR3, OCOOR3, COOR3, CONR3R4, OCONR3R4, $(C_1-C_6)$-alkylene-OR3, $(C_1-C_6)$-alkylene-NR3R4, $(C_1-C_6)$-alkylene-NR3SO₂R4, $(C_1-C_6)$-alkylene-SR3, alkylene-S(O)R3, alkylene-S(O)₂R3, alkylene-S(O)₂NR3R4, $(C_1-C_6)$-alkylene-COR3, $(C_1-C_6)$-alkylene-COOR3, $(C_1-C_6)$-alkylene-CONR3R4, SR3, SOR3, SO₂R3, SO₂NR3R4, NR3SO₂R4, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl;

R3, R4 are each, independently of one another, H, $(C_1-C_6)$-alkyl, $-CF_3$, $(C_3-C_{10})$-cycloalkyl, $(C_6-C_{10})$-aryl, heterocyclyl, $(C_1-C_6)$-alkylene-CONR5R6, CONR5R6, $(C_1-C_6)$-alkylene-COOR5, COOR5, COR5, $(C_1-C_6)$-alkylene-COR5, $(C_1-C_6)$-alkylene-OR5, $(C_1-C_6)$-alkylene-NR5R6, $(C_1-C_6)$-alkylene-SR5, $(C_1-C_6)$-alkylene-S(O)R5, $(C_1-C_6)$-alkylene-S(O)₂R5, S(O)R5, S(O)₂R5, $(C_1-C_4)$-alkylene-$(C_6-C_{10})$-aryl, or $(C_1-C_4)$-alkylene-heterocyclyl, R5, R6 are each, independently of one another, H, $(C_1-C_6)$-alkyl, $(C_1-C_6)$-alkylene-$(C_6-C_{10})$-aryl, $-(C_6-C_{10})$-aryl, heterocyclyl or $(C_1-C_6)$-alkylene-heterocyclyl;

and pharmaceutically acceptable salts thereof.

Preference is further given to compounds of the formula I in which one or more radicals mean R1 is H;

R2 is $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, heterocyclyl, COR3, COOR3, CONR3R4, CN, wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, SH, $SF_5$, OH, $(C_1-C_6)$-alkyl, $-CF_3$, $(C_2-C_6)$-alkenyl, $(C_2-C_6)$-alkynyl, OR3, $OP(O)(OR3)_2$, NR3R4, NR3CONR3R4, COR3, OCOR3, OCOOR3, COOR3, CONR3R4, OCONR3R4, $(C_1-C_6)$-alkylene-OR3, $(C_1-C_6)$-alkylene-NR3R4, $(C_1-C_6)$-alkylene-NR3SO₂R4, $(C_1-C_6)$-alkylene-SR3, alkylene-S(O)R3, alkylene-S(O)₂R3, alkylene-S(O)₂NR3R4, $(C_1-C_6)$-alkylene-COR3, $(C_1-C_6)$-alkylene-COOR3, $(C_1-C_6)$-alkylene-CONR3R4, SR3, SOR3, SO₂R3, SO₂NR3R4, NR3SO₂R4, $(C_1-C_6)$-alkylene-$(C_3-C_{10})$-Cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl;

R3, R4 are each, independently of one another, H, $(C_1-C_6)$-alkyl, —$CF_3$, $(C_3-C_{10})$-cycloalkyl, $(C_6-C_{10})$-aryl, heterocyclyl, $(C_1-C_6)$-alkylene-CONR5R6, CONR5R6, $(C_1-C_6)$-alkylene-COOR5, COOR5, COR5, $(C_1-C_6)$-alkylene-COR5, $(C_1-C_6)$-alkylene-OR5, $(C_1-C_6)$-alkylene-NR5R6, $(C_1-C_6)$-alkylene-SR5, $(C_1-C_6)$-alkylene-S(O)R5, $(C_1-C_6)$-alkylene-S(O)$_2$R5, S(O)R5, S(O)$_2$R5, $(C_1-C_4)$-alkylene-$(C_6-C_{10})$-aryl, or $(C_1-C_4)$-alkylene-heterocyclyl;

R5, R6 are each, independently of one another, H, $(C_1-C_6)$-alkyl, $(C_1-C_6)$-alkylene-$(C_6-C_{10})$-aryl, —$(C_6-C_{10})$-aryl, heterocyclyl or $(C_1-C_6)$-alkylene-heterocyclyl;

and pharmaceutically acceptable salts thereof.

Preference is further given to compounds of the formula I in which one or more radicals mean R1 is H;

R2 is $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, a pyrrolidino, piperidino, hexamethyleneimino, morpholino, piperazino, thiomorpholino or homopiperazino radical; where said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, a pyrrolidino, piperidino, hexamethyleneimtino, morpholino, piperazino, thiomorpholino and homopiperazino radicals are optionally substituted one or more times by F, Cl, Br, CN, $SF_5$, OH, $(C_1-C_6)$-alkyl, —$CF_3$, $(C_2-C_6)$-alkenyl, OR3, NR3R4, NR3CONR3R4, COR3, OCOR3, $CO_2R3$, CONR3R4, OCONR3R4, $(C_1-C_6)$-alkylene-OR3, $(C_1-C_6)$-alkylene-NR3R4, $(C_1-C_6)$-alkylene-NR3SO$_2$R4, $(C_1-C_6)$-alkylene-SR3, alkylene-S(O)R3, alkylene-S(O)$_2$R3, alkylene-S(O)$_2$NR3R4, $(C_1-C_6)$-alkylene-COR3, $(C_1-C_6)$-alkylene-CO$_2$R3, $(C_1-C_6)$-alkylene-CONR3R4, SR3, SOR3, SO$_2$R3, SO$_2$NR3R4, NR3SO$_2$R4, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl, or heterocyclyl, wherein said $(C_6-C_{10})$-aryl is optionally substituted one or more times by F, Cl, Br, I, CN, OH, —$CF_3$, $(C_1-C_6)$-alkyl, OR3, NR3R4, COR3, $C0_2R3$ or CONR3R4, and wherein said heterocyclyl is optionally substituted one or more times by F, Cl, Br, CN, $NO_2$, OH, —$CF_3$, $(C_1-C_6)$-alkyl, OR3, NR3R4, COR3, CO2R3 or CONR3R4;

R3, R4 are each, independently of one another, H, $(C_1-C_6)$-alkyl, —$CF_3$, $(C_3-C_{10})$-cycloalkyl, $(C_6-C_{10})$-aryl, heterocyclyl, $(C_1-C_6)$-alkylene-CONR5R6, $(C_1-C_6)$-alkylene-COOR5, $(C_1-C_6)$-alkylene-COR5, $(C_1-C_6)$-alkylene-OR5, $(C_1-C_6)$-alkylene-NR5R6, $(C_1-C_6)$-alkylene-SR5, $(C_1-C_6)$-alkylene-S(O)R5, $(C_1-C_6)$-alkylene-S(O)$_2$R5, $(C_1-C_4)$-alkylene-$(C_6-C_{10})$-aryl or $(C_1-C_4)$-alkylene-heterocyclyl;

R5, R6 are each, independently of one another, H, $(C_1-C_6)$-alkyl, $(C_3-C_{10})$-cycloalkyl, $(C_1-C_6)$-alkylene-$(C_6-C_{10})$-aryl, —$(C_6-C_{10})$-aryl, heterocyclyl or $(C_1-C6)$-alkylene-$(C_3-C_{10})$-heterocyclyl;

and pharmaceutically acceptable salts thereof.

Preference is further given to compounds of the formula I in which one or more radicals mean R1 is H;

R2 is $(C_1-C_{10})$-alkyl, $(C_3-C_{10})$-cycloalkyl, phenyl, $(C_1-C_6)$-alkylene-phenyl, a pyrrolidino, piperidino, hexamethyleneimino, morpholino, piperazino, thiomorpholino or homopiperazino radical;

and pharmaceutically acceptable salts thereof.

The invention relates to compounds of the formula I in the form of all their stereoisomeric forms such as racemates, racemic and enantiomeric mixtures and pure enantiomers and diastereomers.

Compounds of the formula I,

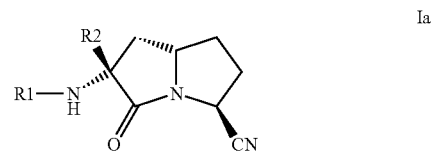

which have the indicated diastereomic form Ia are particularly preferred.

The invention relates to compounds of the formula I in the form of all their stereoisomeric forms such as racemates, racemic and enantiomeric mixtures and pure enantiomers and diastereomers.

If radicals or substituents may occur more than once in the compounds of formula I, they may all, independently of one another, have the stated meaning and be identical or different.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention, as described, for example, in H. Okada et al., Chem. Pharm. Bull. 1994, 42, 57–61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

An alkyl radical means a straight-chain or branched hydrocarbon chain having one or more carbons, such as, for example, methyl, ethyl, propyl, butyl, hexyl, isopropyl, isobutyl, neopentyl, tert-butyl, hexyl.

The alkyl radicals may be substituted one or more times by suitable groups such as, for example: F, Cl, Br, I, $CF_3$, $NO_2$, $N_3$, CN, COOH, COO($C_1$–$C_6$)alkyl, $CONH_2$, CONH($C_1$–$C_6$)alkyl, CON[($C_1$–$C_6$)alkyl]$_2$, cycloalkyl, ($C_2$–$C_6$)-alkenyl, ($C_2$–$C_6$)-alkynyl, aryl, heterocyclyl, O—($C_1$–$C_6$)-alkyl, O—COO—($C_1$–$C_6$)-alkyl, O—CO—($C_1$–$C_6$)-alkyl, O—CO—($C_1$–$C_6$)-aryl, O—CO—($C_1$–$C_6$)-heterocyclyl, $PO_3H_2$, P(O)(O alkyl)2, ($C_1$–$C_6$)-alkylene-P(O)(O alkyl)2, O—P(O)(OH)$_2$, O—P(O)(O alkyl)2, $SO_3H$, $SO_2$—$NH_2$, $SO_2NH(C_1$–$C_6)$-alkyl, $SO_2N[(C_1$–$C_6)$-alkyl]$_2$, S—($C_1$–$C_6$)-alkyl, S—$(CH_2)_n$-aryl, S—$(CH_2)_n$-heterocyclyl, SO—($C_1$–$C_6$)-alkyl, SO—$(CH_2)_n$-aryl, SO—$(CH_2)_n$-heterocyclyl, $SO_2$—($C_1$–$C_6$)-alkyl, $SO_2$—$(CH_2)_n$-aryl, $SO_2$—$(CH_2)_n$-heterocyclyl, $SO_2$—NH$(CH_2)_n$-aryl, $SO_2$—NH$(CH_2)_n$-heterocyclyl, $SO_2$—N[(($C_1$–$C_6$)-alkyl)$(CH_2)_n$-aryl], $SO_2$—N[(($C_1$–$C_6$)-alkyl)$(CH_2)_n$-heterocyclyl], $SO_2$—N$((CH_2)_n$-aryl)$_2$, $SO_2$—N$((CH_2)_n$-(heterocyclyl))$_2$, where n can be 0–6, and the aryl or heterocyclyl radical may be substituted up to three times by F, Cl, Br, OH, $CF_3$, $SF_5$, $NO_2$, CN, $OCF_3$, O—($C_1$–$C_6$)-alkyl, ($C_1$–$C_6$)-alkyl, $NH_2$; $C(NH)(NH_2)$, $NH_2$, NH—($C_1$–$C_6$)-alkyl, N(($C_1$–$C_6$)-alkyl)$_2$, NH($C_1$–$C_7$)-acyl, NH—CO—($C_1$–$C_6$)-alkyl, NH—COO—($C_1$–$C_6$)-alkyl, NH—CO-aryl, NH—CO-heterocyclyl, NH—COO-aryl, NH—COO-heterocyclyl, NH—CO—NH—($C_1$–$C_6$)-alkyl, NH—CO—NH-aryl, NH—CO—NH-heterocyclyl, N[($C_1$–$C_6$)-alkyl]-CO—($C_1$–$C_6$)-alkyl, N[($C_1$–$C_6$)-alkyl]-COO—($C_1$–$C_6$)-alkyl, N[($C_1$–$C_6$)-alkyl]-CO-aryl, N[($C_1$–$C_6$)-alkyl]-CO-heterocyclyl, N[($C_1$–$C_6$)-alkyl]-COO-aryl, N[($C_1$–$C_6$)-alkyl]-COO-heterocyclyl, N[($C_1$–$C_6$)-alkyl]-CO-NH-($C_1$–$C_6$)-alkyl), N[($C_1$–$C_6$)-alkyl]-CO—NH-aryl, N[($C_1$–$C_6$)-alkyl]-CO—NH-heterocyclyl, N[($C_1$–$C_6$)-alkyl]-CO—N($C_1$–$C_6$)-alkyl)$_2$, N[($C_1$–$C_6$)-alkyl]-CO—N(($C_1$–$C_6$)-alkyl)-aryl, N[($C_1$–$C_6$)-alkyl]-CO—N($C_1$–$C_6$)-alkyl)-heterocyclyl, N[($C_1$–$C_6$)-alkyl]-CO—N(aryl)$_2$, N[($C_1$–$C_6$)-alkyl]-CO—N(heterocyclyl)$_2$, N(aryl)-CO—($C_1$–$C_6$)-alkyl, N(heterocyclyl)-CO—($C_1$–$C_6$)-alkyl, N(aryl)-COO—($C_1$–$C_6$)-alkyl, N(heterocyclyl)-COO—($C_1$–$C_6$)-alkyl, N(aryl)-CO-aryl, N(heterocyclyl)-CO-aryl, N(aryl)-COO-aryl, N(heterocyclyl)-COO-aryl, N(aryl)-CO—NH—($C_1$–$C_6$)-alkyl), N(heterocyclyl)-CO—NH—($C_1$–$C_6$)-alkyl), N(aryl)-CO—NH-aryl, N(heterocyclyl)-CO—NH-aryl, N(aryl)-CO—N(($C_1$–$C_6$)-alkyl)$_2$, N(heterocyclyl)-CO—N(($C_1$–$C_6$)-alkyl)$_2$, N(aryl)-CO—N(($C_1$–$C_6$)-alkyl)-aryl, N(heterocyclyl)-CO—N(($C_1$–$C_6$)-alkyl)-aryl, N(aryl)-CO—N(aryl)$_2$, N(heterocyclyl)-CO—N-(aryl)$_2$, aryl, O—$(CH_2)_n$-aryl, O—$(CH_2)_n$-heterocyclyl, where n may be 0–6, where the aryl or heterocyclyl radical may be substituted one to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SF_5$, $SO_2$—$CH_3$, COOH, COO—($C_1$–$C_6$)-alkyl, $CONH_2$.

An alkynyl radical means a straight-chain or branched hydrocarbon chain having two or more carbons and one or more triple bonds, such as, for example, ethynyl, propynyl, hexynyl.

The alkynyl radicals may be substituted one or more times by suitable groups such as, for example: F, Cl, Br, I, $CF_3$, $NO_2$, $N_3$, CN, COOH, COO($C_1$–$C_6$)alkyl, $CONH_2$, CONH($C_1$–$C_6$)alkyl, CON[($C_1$–$C_6$)alkyl]$_2$, cycloalkyl, ($C_2$–$C_6$)-alkenyl, ($C_1$–$C_6$)-alkyl, O—($C_1$–$C_6$)-alkyl O—CO—($C_1$–$C_6$)-alkyl, O—CO—($C_1$–$C_6$)-Aryl, O—CO—($C_1$–$C_6$)-heterocyclyl; $PO_3H_2$, P(O)(O alkyl)2, (C1–C6)-alkylene-P(O)(O alkyl)2, O—P(O)(OH)$_2$, O—P(O)(O alkyl)2, $SO_3H$, $SO_2$—$NH_2$, $SO_2NH(C_1$–$C_6)$-alkyl, $SO_2N[(C_1$–$C_6)$-alkyl]$_2$, S—($C_1$–$C_6$)-alkyl, S—$(CH_2)_n$-aryl, S—$(CH_2)_n$-heterocyclyl, SO—($C_1$–$C_6$)-alkyl, SO—$(CH_2)_n$-aryl, SO—$(CH_2)_n$-heterocyclyl, $SO_2$—($C_1$–$C_6$)-alkyl, $SO_2$—$(CH_2)_n$-aryl, $SO_2$—$(CH_2)_n$-heterocyclyl, $SO_2$—NH$(CH_2)_n$-aryl, $SO_2$—NH$(CH_2)_n$-heterocyclyl, $SO_2$—N(($C_1$–$C_6$)-alkyl)$(CH_2)_n$-aryl, $SO_2$—N(($C_1$–$C_6$)-alkyl)$(CH_2)_n$-heterocyclyl, $SO_2$—N$((CH_2)_n$-aryl)$_2$, $SO_2$—N$((CH_2)_n$-(heterocyclyl))$_2$ where n may be 0–6 and the aryl radical or the heterocyclic radical may be substituted up to twice by F, Cl, Br, OH, $CF_3$, $SF_5$, $NO_2$, CN, $OCF_3$, O—($C_1$–$C_6$)-alkyl, ($C_1$–$C_6$)-alkyl, $NH_2$; $C(NH)(NH_2)$, $NH_2$, NH—($C_1$–$C_6$)-alkyl, N(($C_1$–$C_6$)-alkyl)$_2$, NH($C_1$–$C_7$)-acyl, NH—CO—($C_1$–$C_6$)-alkyl, NH—COO—($C_1$–$C_6$)-alkyl, NH—CO-aryl, NH—CO-heterocyclyl, NH—COO-aryl, NH—COO-heterocyclyl, NH—CO—NH—($C_1$–$C_6$)-alkyl, NH—CO—NH-aryl, NH—CO—NH-heterocyclyl, N[($C_1$–$C_6$)-alkyl]-CO—($C_1$–$C_6$)-alkyl, N[($C_1$–$C_6$)-alkyl]-COO—($C_1$–$C_6$)-alkyl, N[($C_1$–$C_6$)-alkyl]-CO-aryl, N[($C_1$–$C_6$)-alkyl]-CO-heterocyclyl, N[($C_1$–$C_6$)-alkyl]-COO-aryl, N[($C_1$–$C_6$)-alkyl]-COO-heterocyclyl, N[($C_1$–$C_6$)-alkyl]-CO—NH—($C_1$–$C_6$)-alkyl), N[($C_1$–$C_6$)-alkyl]-CO—NH-aryl, N[($C_1$–$C_6$)-alkyl]-CO—NH-heterocyclyl, N[($C_1$–$C_6$)-alkyl]-CO—N—(($C_1$–$C_6$)-alkyl)$_2$, N[($C_1$–$C_6$)-alkyl]-CO—N(($C_1$–$C_6$)-alkyl)-aryl, N[($C_1$–$C_6$)-alkyl]-CO—N(($C_1$–$C_6$)-alkyl)-heterocyclyl, N[($C_1$–$C_6$)-alkyl]-CO—N(aryl)$_2$, N[($C_1$–$C_6$)-alkyl]-CO—N(heterocyclyl)$_2$, N(aryl)-CO—($C_1$–$C_6$)-alkyl, N(heterocyclyl)-CO—($C_1$–$C_6$)-alkyl, N(aryl)-COO—($C_1$–$C_6$)-alkyl, N(heterocyclyl)-COO—($C_1$–$C_6$)-alkyl, N(aryl)-CO-aryl, N(heterocyclyl)-CO-aryl, N(aryl)-COO-aryl, N(heterocyclyl)-COO-aryl, N(aryl)-CO—NH—($C_1$–$C_6$)-alkyl), N(heterocyclyl)-CO—NH—($C_1$–$C_6$)-alkyl), N(aryl)-CO—NH-aryl, N(heterocylyl)-CO—NH-aryl, N(aryl)-CO—N(($C_1$–$C_6$)-alkyl)$_2$, N(heterocyclyl)-CO—N—(($C_1$–$C_6$)-alkyl)$_2$, N(aryl)-CO—N[($C_1$–$C_6$)-alkyl]-aryl, N(heterocyclyl)-CO—N[($C_1$–$C_6$)-alkyl]-aryl, N(aryl)-CO—N(aryl)$_2$, N(heterocyclyl)-CO—N-(aryl)$_2$, aryl, O—$(CH_2)_n$-aryl, O—$(CH_2)_n$-heterocyclyl, where n may be 0–6, where the aryl or heterocyclyl radical may be substituted one to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SF_5$, $SO_2$—$CH_3$, COOH, COO—($C_1$–$C_6$)-alkyl, $CONH_2$.

An alkenyl radical means a straight-chain or branched hydrocarbon chain having two or more carbons and one or more double bonds, such as, for example, vinyl, allyl, pentenyl. The alkenyl radicals may be substituted one or more times by suitable groups such as, for example: F, Cl, Br, I, $CF_3$, $NO_2$, $N_3$, CN, COOH, COO($C_1$–$C_6$)alkyl, $CONH_2$, CONH($C_1$–$C_6$)alkyl, CON[($C_1$–$C_6$)alkyl]$_2$, cycloalkyl, ($C_1$–$C_1$)-alkyl, ($C_2$–$C_6$)-alkynyl, aryl, heterocyclyl, aryl, $SO_2-N((C_1-C_6)\text{-alkyl})(CH_2)_n\text{-heterocyclyl}$, $SO_2-N((CH_2)_n\text{-aryl})_2$, $SO_2-N((CH_2)_n\text{-(heterocyclyl)})_2$ where n may be 0–6 and the aryl radical or the heterocyclyl radical may be substituted up to twice by F, Cl, Br, OH, $CF_3$, $SF_5$, $NO_2$, CN, $OCF_3$, $O-(C_1-C_6)$-alkyl, $(C_1-C_6)$-alkyl, $NH_2$;
$C(NH)(NH_2)$, $NH_2$, $NH-(C_1-C_6)$-alkyl, $N((C_1-C_6)\text{-alkyl})_2$, $NH(C_1-C_7)$-acyl, $NH-CO-(C_1-C_6)$-alkyl, $NH-COO-(C_1-C_6)$-alkyl, NH—CO-aryl, NH—CO-heterocyclyl, NH—COO-aryl, NH—COO-heterocyclyl, $NH-CO-NH-(C_1-C_6)$-alkyl, NH—CO—NH-aryl, NH—CO—NH-heterocyclyl, $N[(C_1-C_6)\text{-alkyl}]-CO-(C_1-C_6)$-alkyl, $N[(C_1-C_6)\text{-alkyl}]-COO-(C_1-C_6)$-alkyl, $N[(C_1-C_6)\text{-alkyl}]$-CO-aryl, $N[(C_1-C_6)\text{-alkyl}]$-CO-heterocyclyl, $N[(C_1-C_6)\text{-alkyl}]$-COO-aryl, $N[(C_1-C_6)\text{-alkyl}]$-COO-heterocyclyl, $N[(C_1-C_6)\text{-alkyl}]-CO-NH-(C_1-C_6)$-alkyl), $N[(C_1-C_6)\text{-alkyl}]$-CO—NH-aryl, $N[(C_1-C_6)\text{-alkyl}]$-CO—NH-heterocyclyl, $N[(C_1-C_6)\text{-alkyl}]-CO-N((C_1-C_6)\text{-alkyl})_2$, $N[(C_1-C_6)\text{-alkyl}]-CO-N((C_1-C_6)\text{-alkyl})$-aryl, $N[(C_1-C_6)\text{-alkyl}]-CO-N((C_1-C_6)\text{-alkyl})$-heterocyclyl, $N[(C_1-C_6)\text{-alkyl}]-CO-N(\text{aryl})_2$, $N[(C_1-C_6)\text{-alkyl}]-CO-N(\text{heterocyclyl})_2$, $N(\text{aryl})-CO-(C_1-C_6)$-alkyl, $N(\text{heterocyclyl})-CO-(C_1-C_6)$-alkyl, $N(\text{aryl})-COO-(C_1-C_6)$-alkyl, $N(\text{heterocyclyl})-COO-(C_1-C_6)$-alkyl, N(aryl)-CO-aryl, N(heterocyclyl)-CO-aryl, N(aryl)-COO-aryl, N(heterocyclyl)-COO-aryl, $N(\text{aryl})-CO-NH-(C_1-C_6)$-alkyl, $N(\text{heterocyclyl})-CO-NH-(C_1-C_6)$-alkyl, N(aryl)-CO—NH-aryl, N(heterocyclyl)-CO—NH-aryl, $N(\text{aryl})-CO-N((C_1-C_6)\text{-alkyl})_2$, $N(\text{heterocyclyl})-CO-N((C_1-C_6)\text{-alkyl})_2$, $N(\text{aryl})-CO-N[(C_1-C_6)\text{-alkyl}]$-aryl, $N(\text{heterocyclyl})-CO-N[(C_1-C_6)\text{-alkyl}]$-aryl, $N(\text{aryl})-CO-N(\text{aryl})_2$, $N(\text{heterocyclyl})-CO-N(\text{aryl})_2$, aryl, $O-(CH_2)_n$-aryl, $O-(CH_2)_n$-heterocyclyl where n may be 0–6, where the aryl or heterocyclyl radical may be substituted one to 3 times by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)\text{-alkyl})_2$, $SF_5$, $SO_2-CH_3$, COOH, $COO-(C_1-C_6)$-alkyl, $CONH_2$.

An aryl radical means a phenyl, naphthyl, biphenyl, tetrahydronaphthyl, alpha- or beta-tetralon-, indanyl- or indan-1-on-yl radical.

The aryl radicals may be substituted one or more times by suitable groups such as, for example: F, Cl, Br, I, $CF_3$, $NO_2$, $SF_5$, $SO_2-CH_3$, COOH, $COO-(C_1-C_6)$-alkyl, $CONH_2$, $CONH(C_1-C_6)$alkyl, $CON[(C_1-C_6)\text{alkyl}]_2$, cycloalkyl, $(C_1-C_{10})$-alkyl, $(C_2-C_6)$-alkenyl, $(C_2-C_6)$-alkynyl $O-(C_1-C_6)$-alkyl $O-CO-(C_1-C_6)$-alkyl, $O-CO-(C_1-C_6)$-aryl, $O-CO-(C_1-C_6)$-heterocyclyl;

$PO_3H_2$, P(O)(O alkyl)2, (C1–C6)-alkylene-P(O)(O alkyl)2, $O-P(O)(OH)_2$, O—P(O)(O alkyl)2, $SO_3H$, $SO_2-NH_2$, $SO_2NH(C_1-C_6)$-alkyl, $SO_2N[(C_1-C_6)\text{-alkyl}]_2$, $S-(C_1-C_6)$-alkyl, $S-(CH_2)_n$-aryl, $S-(CH_2)_n$-heterocyclyl, $SO-(C_1-C_6)$-alkyl, $SO-(CH_2)_n$-aryl, $SO-(CH_2)_n$-heterocyclyl, $SO_2-(C_1-C_6)$-alkyl, $SO_2-(CH_2)_n$-aryl, $SO_2-(CH_2)_n$-heterocyclyl, $SO_2-NH(CH_2)_n$-aryl, $SO_2-NH(CH_2)_n$-heterocyclyl, $SO_2-N((C_1-C_6)\text{-alkyl})(CH_2)_n$-aryl, $SO_2-N((C_1-C_6)\text{-alkyl})(CH_2)_n$-heterocyclyl, $SO_2-N((CH_2)_n\text{-aryl})_2$, $SO_2-N((CH_2)_n\text{-(heterocyclyl)})_2$ where n may be 0–6 and the aryl radical or the heterocyclic radical may be substituted up to twice by F, Cl, Br, OH, $CF_3$, $NO_2$, $SF_5$, CN, $OCF_3$, $O-(C_1-C_6)$-alkyl, $(C_1-C_6)$-alkyl, $NH_2$;
$C(NH)(NH_2)$, $NH_2$, $NH-(C_1-C_6)$-alkyl, $N((C_1-C_6)\text{-alkyl})_2$, $NH(C_1-C_7)$-acyl, $NH-CO-(C_1-C_6)$-alkyl, $NH-COO-(C_1-C_6)$-alkyl, NH—CO-aryl, NH—CO-heterocyclyl, NH—COO-aryl, NH—COO-heterocyclyl, $NH-CO-NH-(C_1-C_6)$-alkyl), NH—CO—NH-aryl, NH—CO—NH-heterocyclyl, $N[(C_1-C_6)\text{-alkyl}]-CO-(C_1-C_6)$-alkyl, $N[(C_1-C_6)\text{-alkyl}]-COO-(C_1-C_6)$-alkyl, $N[(C_1-C_6)\text{-alkyl}]$-CO-aryl, $N[(C_1-C_6)\text{-alkyl}]$-CO-heterocyclyl, $N[(C_1-C_6)\text{-alkyl}]$-COO-aryl, $N[(C_1-C_6)\text{-alkyl}]$-COO-heterocyclyl, $N[(C_1-C_6)\text{-alkyl}]-CO-NH-(C_1-C_6)$-alkyl), $N[(C_1-C_6)\text{-alkyl}]$-CO—NH-aryl, $N[(C_1-C_6)\text{-alkyl}]$-CO—NH-heterocyclyl, $N[(C_1-C_6)\text{-alkyl}]-CO-N((C_1-C_6)\text{-alkyl})_2$, $N[(C_1-C_6)\text{-alkyl}]-CO-N((C_1-C_6)\text{-alkyl})$-aryl, $N[(C_1-C_6)\text{-alkyl}]-CO-N((C_1-C_6)\text{-alkyl})$-heterocyclyl, $N[(C_1-C_6)\text{-alkyl}]-CO-N(\text{aryl})_2$, $N[(C_1-C_6)\text{-alkyl}]-CO-N(\text{heterocyclyl})_2$, $N(\text{aryl})-CO-(C_1-C_6)$-alkyl, $N(\text{heterocyclyl})-CO-(C_1-C_6)$-alkyl, $N(\text{aryl})-COO-(C_1-C_6)$-alkyl, $N(\text{heterocyclyl})-COO-(C_1-C_6)$-alkyl, N(aryl)-CO-aryl, N(heterocyclyl)-CO-aryl, N(aryl)-COO-aryl, N(heterocyclyl)-COO-aryl, $N(\text{aryl})-CO-NH-(C_1-C_6)$-alkyl, $N(\text{heterocyclyl})-CO-NH-(C_1-C_6)$-alkyl, N(aryl)-CO—NH-aryl, N(heterocyclyl)-CO—NH-aryl, $N(\text{aryl})-CO-N((C_1-C_6)\text{-alkyl})_2$, $N(\text{heterocyclyl})-CO-N((C_1-C_6)\text{-alkyl})_2$, $N(\text{aryl})-CO-N[(C_1-C_6)\text{-alkyl}]$-aryl, $N(\text{heterocyclyl})-CO-N[(C_1-C_6)\text{-alkyl}]$-aryl, $N(\text{aryl})-CO-N(\text{aryl})_2$, $N(\text{heterocyclyl})-CO-N(\text{aryl})_2$, aryl, $O-(CH_2)_n$-aryl, $O-(CH_2)_n$-heterocyclyl, where n may be 0–6, where the aryl or heterocyclyl radical may be substituted one to 3 times by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)\text{-alkyl})_2$, $SF_5$, $SO_2-CH_3$, COOH, $COO-(C_1-C_6)$-alkyl, $CONH_2$.

A cycloalkyl radical means a ring system which comprises one or more rings and which is unsaturated or partially unsaturated (with one or two double bonds), and which is composed exclusively of carbon atoms, for example, cyclopropyl, cyclopentyl, cyclopentenyl, cyclohexyl or adamantyl.

The cycloalkyl radicals radicals may be substituted one or more times by suitable groups such as, for example: F, Cl, Br, I, $CF_3$, $NO_2$, $N_3$, CN, COOH, $COO(C_1-C_6)$alkyl, $CONH_2$, $CONH(C_1-C_6)$alkyl, $CON[(C_1-C_6)\text{alkyl}]_2$, cycloalkyl, $(C_1-C_{10})$-alkyl, $(C_2-C_6)$-alkenyl, $(C_2-C_6)$-alkynyl $O-(C_1-C_6)$-alkyl $O-CO-(C_1-C_6)$-alkyl, $O-CO-(C_1-C_6)$-Aryl, $O-CO-(C_1-C_6)$-heterocyclyl;

$PO_3H_2$, P(O)(O alkyl)2, (C1–C6)-alkylene-P(O)(O alkyl)2, $O-P(O)(OH)_2$, O—P(O)(O alkyl)2, $SO_3H$, $SO_2-NH_2$, $SO_2NH(C_1-C_6)$-alkyl, $SO_2N[(C_1-C_6)\text{-alkyl}]_2$, $S-(C_1-C_6)$-alkyl, $S-(CH_2)_n$-aryl, $S-(CH_2)_n$-heterocyclyl, $SO-(C_1-C_6)$-alkyl, $SO-(CH_2)_n$-aryl, $SO-(CH_2)_n$-heterocyclyl, $SO_2-(C_1-C_6)$-alkyl, $SO_2-(CH_2)_n$-aryl, $SO_2-(CH_2)_n$-heterocyclyl, $SO_2-NH(CH_2)_n$-aryl, $SO_2-NH(CH_2)_n$-heterocyclyl, $SO_2-N((C_1-C_6)\text{-alkyl})(CH_2)_n$-aryl, $SO_2-N((C_1-C_6)\text{-alkyl})(CH_2)_n$-heterocyclyl, $SO_2-N((CH_2)_n\text{-aryl})_2$, $SO_2-N((CH_2)_n\text{-(heterocyclyl)})_2$ where n may be 0–6 and the aryl radical or the heterocyclyl radical may be substituted up to twice by F, Cl, Br, OH, $CF_3$, $SF_5$, $NO_2$, CN, $OCF_3$, $O-(C_1-C_6)$-alkyl, $(C_1-C_6)$-alkyl, $NH_2$;
$C(NH)(NH_2)$, $NH_2$, $NH-(C_1-C_6)$-alkyl, $N((C_1-C_6)\text{-alkyl})_2$, $NH(C_1-C_7)$-acyl, $NH-CO-(C_1-C_6)$-alkyl, $NH-COO-(C_1-C_6)$-alkyl, NH—CO-aryl, NH—CO-heterocyclyl, NH—COO-aryl, NH—COO-heterocyclyl, $NH-CO-NH-(C_1-C_6)$-alkyl), NH—CO—NH-aryl, NH—CO—NH-heterocyclyl, $N[(C_1-C_6)\text{-alkyl}]-CO-(C_1-C_6)$-alkyl, $N[(C_1-C_6)\text{-alkyl}]-COO-(C_1-C_6)$-alkyl, $N[(C_1-C_6)\text{-alkyl}]$-CO-aryl, $N[(C_1-C_6)\text{-alkyl}]$-CO-heterocyclyl, $N[(C_1-C_6)\text{-alkyl}]$-COO-aryl, $N[(C_1-C_6)\text{-alkyl}]$-COO-heterocyclyl, $N[(C_1-C_6)\text{-alkyl}]-CO-NH-(C_1-C_6)$-alkyl), $N[(C_1-C_6)\text{-alkyl}]$-CO—NH-aryl, $N[(C_1-C_6)\text{-alkyl}]$-CO—NH-heterocyclyl, $N[(C_1-C_6)$- alkyl]-CO—N((C$_1$–C$_6$)-alkyl)$_2$, N[(C$_1$–C$_6$)-alkyl]-CO—N((C$_1$–C$_6$)-alkyl)-aryl, N[(C$_1$–C$_6$)-alkyl]-CO—N((C$_1$–C$_6$)-alkyl)-heterocyclyl, N[(C$_1$–C$_6$)-alkyl]-CO—N(aryl)$_2$, N[(C$_1$–C$_6$)-alkyl]-CO—N(heterocyclyl)$_2$, N(aryl)-CO—(C$_1$–C$_6$)-alkyl, N(heterocyclyl)-CO—(C$_1$–C$_6$)-alkyl, N(aryl)-COO—(C$_1$–C$_6$)-alkyl, N(heterocyclyl)-COO—(C$_1$–C$_6$)-alkyl, N(aryl)-CO-aryl, N(heterocyclyl)-CO-aryl, N(aryl)-COO-aryl, N(heterocyclyl)-COO-aryl, N(aryl)-CO—NH—(C$_1$–C$_6$)-alkyl, N(heterocyclyl)-CO—NH—(C$_1$–C$_6$)-alkyl, N(aryl)-CO—NH-aryl, N(heterocyclyl)-CO—NH-aryl, N(aryl)-CO—N((C$_1$–C$_6$)-alkyl)$_2$, N(heterocyclyl)-CO—N((C$_1$–C$_6$)-alkyl)$_2$, N(aryl)-CO—N[(C$_1$–C$_6$)-alkyl]-aryl, N(heterocyclyl)-CO—N[(C$_1$–C$_6$)-alkyl]-aryl, N(aryl)-CO—N(aryl)$_2$, N(heterocyclyl)-CO—N(aryl)$_2$, aryl, O—(CH$_2$)$_n$-aryl, O—(CH$_2$)$_n$-heterocyclyl, where n may be 0–6, where the aryl or heterocyclyl radical may be substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SF$_5$, SO$_2$—CH$_3$, COOH, COO—(C$_1$–C$_6$)-alkyl, CONH$_2$.

Heterocycle or heterocyclic radical means rings or ring systems which, apart from carbon, also comprise heteroatoms such as, for example, nitrogen, oxygen or sulfur. Ring systems in which the heterocycle or heterocyclic radical is fused to benzene nuclei are also included in this definition.

Suitable heterocyclyl rings or "heterocyclic radicals" are acridinyl, benzimidazolyl, benzofuryl, benzothienyl, benzothiophenyl, benzoxazolyl, benzthiazolyl, benztriazolyl, benzisoxazolyl, benzisothiazolyl, carbazolyl, 4aH-carbazolyl, carbolinyl,quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl, aziridinyl, azetininyl, azepanyl, azocanyl and xanthenyl.

Pyridyl stands both for 2-, 3- and 4-pyridyl. Thienyl stands both for 2- and 3-thienyl. Furyl stands both for 2- and 3-furyl.

Also included are the corresponding N-oxides of these compounds, that is to say, for example, 1-oxy-2-, 3- or 4-pyridyl.

Also included are derivatives of these heterocycles which are benzo-fused one or more times.

The heterocyclic rings or heterocyclic radicals may be substituted one or more times by suitable groups such as, for example: F, Cl, Br, I, CF$_3$, NO$_2$, N$_3$, CN, COOH, COO(C$_1$–C$_6$)alkyl, CONH$_2$, CONH(C$_1$–C$_6$)alkyl, CON[(C$_1$–C$_6$)alkyl]$_2$, cycloalkyl, (C$_1$–C$_{10}$)-alkyl, (C$_2$–C$_6$)-alkenyl, (C$_2$–C$_6$)-alkynyl, O—(C$_1$–C$_6$)-alkyl O—CO—(C$_1$–C$_6$)-alkyl, O—CO—(C$_1$–C$_6$)-aryl, O—CO—(C$_1$–C$_6$)-heterocyclyl;

PO$_3$H$_2$, P(O)(O alkyl)2, (C1–C6)-alkylene-P(O)(O alkyl)2, O—P(O)(OH)$_2$, O—P(O)(O alkyl)2, SO$_3$H, SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-aryl, S—(CH$_2$)$_n$-heterocyclyl, SO—(C$_1$–C$_6$)-alkyl, SO—(CH$_2$)$_n$-aryl, SO—(CH$_2$)$_n$-heterocyclyl, SO$_2$—(C$_1$–C$_6$)-alkyl, SO$_2$—(CH$_2$)$_n$-aryl, SO$_2$—(CH$_2$)$_n$-heterocyclyl, SO$_2$—NH(CH$_2$)$_n$-aryl, SO$_2$—NH(CH$_2$)$_n$-heterocyclyl, SO$_2$—N(C$_1$–C$_6$)-alkyl)(CH$_2$)$_n$-aryl, SO$_2$—N(C$_1$–C$_6$)-alkyl)(CH$_2$)$_n$-heterocyclyl, SO$_2$—N((CH$_2$)$_n$-aryl)$_2$, , SO$_2$—N((CH$_2$)$_n$-(heterocyclyl)$_2$, where n can be 0–6, and the acyl radical or heterocylic radical may be substituted up to twice by F, Cl, Br, OH, CF$_3$, SF5, NO$_2$, CN, OCF$_3$, O—(C$_1$–C$_6$)-alkyl, (C$_1$–C$_6$)-alkyl, NH$_2$; C(NH)(NH$_2$), NH$_2$, NH—(C$_1$–C$_6$)-alkyl, N((C$_1$–C$_6$)-alkyl)$_2$, NH(C$_1$–C$_7$)-acyl, NH—CO—(C$_1$–C$_6$)-alkyl, NH—COO—(C$_1$–C$_6$)-alkyl, NH—CO-aryl, NH—CO-heterocyclyl, NH—COO-aryl, NH—COO-heterocyclyl, NH—CO—NH—(C$_1$–C$_6$)-alkyl, NH—CO—NH-aryl, NH—CO—NH-heterocyclyl, N[(C$_1$–C$_6$)-alkyl]-CO—(C$_1$–C$_6$)-alkyl, N[(C$_1$–C$_6$)-alkyl]-COO—(C$_1$–C$_6$)-alkyl, N[(C$_1$–C$_6$)-alkyl]-CO-aryl, N[(C$_1$–C$_6$)-alkyl]-CO-heterocyclyl, N[(C$_1$–C$_6$)-alkyl]-COO-aryl, N[(C$_1$–C$_6$)-alkyl]-COO-heterocyclyl, N[(C$_1$–C$_6$)-alkyl]-CO—NH—(C$_1$–C$_6$)-alkyl), N[(C$_1$–C$_6$)-alkyl]-CO—NH-aryl, N[(C$_1$–C$_6$)-alkyl]-CO—NH-heterocyclyl, N[(C$_1$–C$_6$)-alkyl]-CO—N—((C$_1$–C$_6$)-alkyl)$_2$, N[(C$_1$–C$_6$)-alkyl]-CO—N((C$_1$–C$_6$)-alkyl)-aryl, N[(C$_1$–C$_6$)-alkyl]-CO—N((C$_1$–C$_6$)-alkyl)-heterocyclyl, N[(C$_1$–C$_6$)-alkyl]-CO—N-(aryl)$_2$, N[(C$_1$–C$_6$)-alkyl]-CO—N-(heterocyclyl)$_2$, N(aryl)-CO—(C$_1$–C$_6$)-alkyl, N(heterocyclyl)-CO—(C$_1$–C$_6$)-alkyl, N(aryl)-COO—(C$_1$–C$_6$)-alkyl, N(heterocyclyl)-COO—(C$_1$–C$_6$)-alkyl, N(aryl)-CO-aryl, N(heterocyclyl)-CO-aryl, N(aryl)-COO-aryl, N(heterocyclyl)-COO-aryl, N(aryl)-CO—NH—(C$_1$–C$_6$)-alkyl, N(heterocyclyl)-CO—NH—(C$_1$–C$_6$)-alkyl, N(aryl)-CO—NH-aryl, N(heterocyclyl)-CO—NH-aryl, N(aryl)-CO—N-((C$_1$–C$_6$)-alkyl)$_2$, N(heterocyclyl)-CO—N—((C$_1$–C$_6$)-alkyl)$_2$, N(aryl)-CO—N[(C$_1$–C$_6$)-alkyl]-aryl, N(heterocyclyl)-CO—N[(C$_1$–C$_6$)-alkyl]-aryl, N(aryl)-CO—N(aryl)$_2$, N(heterocyclyl)-CO—N(aryl)$_2$, aryl, O—(CH$_2$)$_n$-aryl, O—(CH$_2$)$_n$-heterocyclyl, where n may be 0–6, where the aryl or heterocyclyl radical may be substituted one to 3 times by F, Cl, Br, I, OH, CF$_3$, NO$_2$, CN, OCF$_3$, SF$_5$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SF$_5$, SO$_2$—CH$_3$, COOH, COO—(C$_1$–C$_6$)-alkyl, CONH$_2$.

As used herein:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The compounds of the formula 1 can be prepared by methods known per se. Thus, the tert-butyl ester 3 can be obtained starting from commercially available S-pyroglutamic acid 2 by protection (e.g. with tert-butyl acetate and acid). Compound 4 is obtained therefrom by Boc protection (see also *J. Chem. Soc., Perkin Trans* 1 1996, 507–514). Reaction with suitable reducing agents (e.g. lithium triethylborohydride) affords the aminal 5. Olefination with triethyl phosphonoacetate under basic conditions (e.g. NaH) results in the pyrrolidine 6 (*Tetrahedron* 2000, 4289–4298). This building block can then be converted by reduction (e.g. with lithium borohydride) and oxidation (e.g. Swern Oxidation *J. Org. Chem.* 1976, 41, 957) into the aldehyde 7 (R=H). An alternative to this is to obtain the ketones 7 (R≠H) by reaction to give the Weinreb amide (e.g. with N,O-dimethylhydroxylamine hydrochloride in the presence of trimethylaluminum) and subsequent addition of suitable organometallic reagents (Met=Li, MgX, where X=Cl, Br, I). Subsequent Strecker synthesis (e.g. with benzylamine and trimethylsilyl cyanide) then affords the nitriles 8. The nitrile group is converted into the amide (e.g. with potassium carbonate in a mixture of dimethyl sulfoxide, water and hydrogen peroxide), producing the compounds 9. Hydrolysis (e.g. with sodium hydroxide solution in ethanol) then affords the dicarboxylic acids 10. Hydrogenation (e.g. with hydrogen in the presence of palladium on activated carbon) affords the amino dicarboxylic acids 11. These are then provided with a suitable protective group on the nitrogen (e.g. Pg=benzyloxycarbonyl (Z) by reaction with N-(benzyloxycarbonyloxy)succinimide in the presence of potassium carbonate), resulting in the derivatives 12. The carboxyl groups are esterified to give the compounds 13 (e.g. with trimethylsilyldiazomethane) and then the Boc group is cleaved by reaction with a suitable acid (e.g. trifluoroacetic acid) to give the compounds 14. Cyclization under basic conditions (e.g. diisopropylethylamine in methanol) then affords the bicycles 15. The protective group Pg in 15 is then cleaved (e.g. by hydrogenation with hydrogen in the presence of palladium on activated carbon for Pg=Z) and the amino group is Boc-protected (e.g. with Boc anhydride), resulting in the compounds 16. Reaction thereof with ammonia results in the amides 17 and 18, which can be separated from one another by chromatography. Reaction of 17 with activating reagents (e.g. cyanuric chloride) subsequently affords the nitrites 19, from which the amines 20 are produced by elimination of the Boc group (e.g. with trifluoroacetic acid). Reductive amination of the amino group by conventional processes results in the compounds 21.

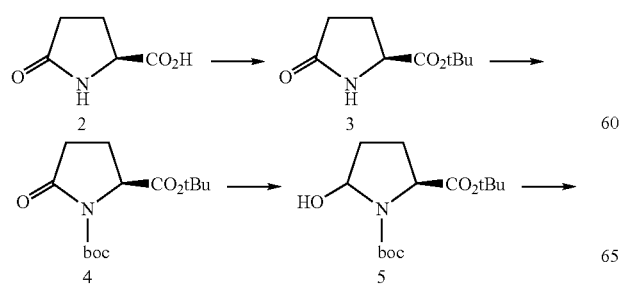

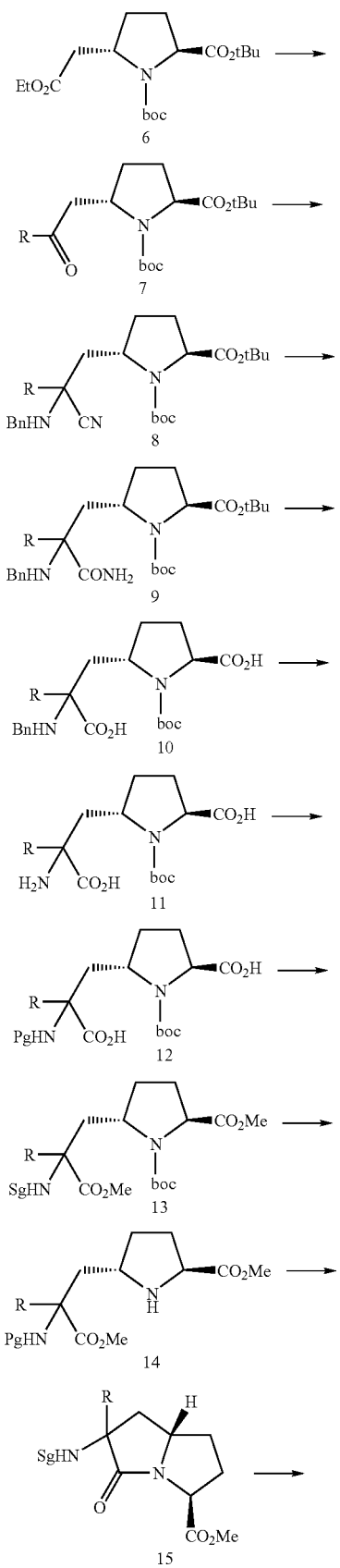

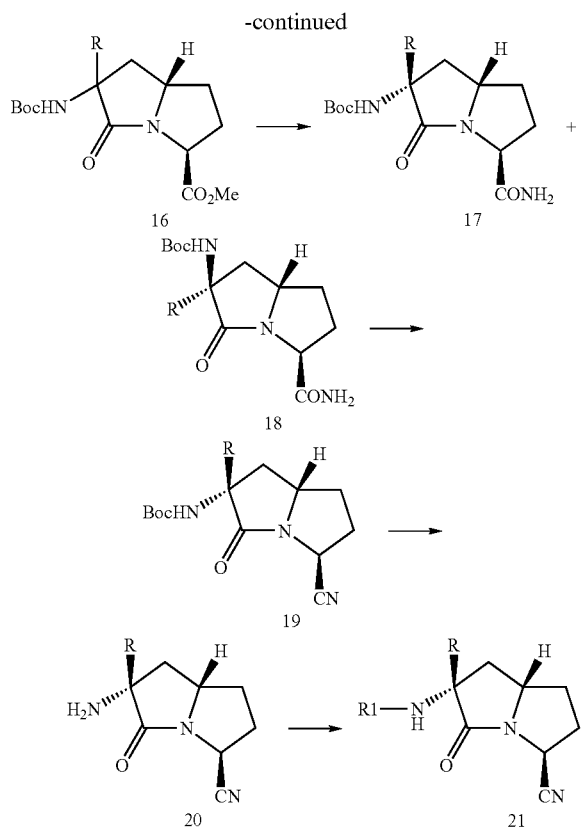

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day and per kilogram of bodyweight, for example 3–10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of formula (I) may also be administered in combination with other active ingredients.

Further active ingredients suitable for combination products are:

all antidiabetics mentioned in the Rote Liste 2003, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 97/26265, WO 99/03861, WO 01/04156, WO 00/34331, WO 00/34332, WO 91/11457 and U.S. Pat. No. 6,380,357 and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside, or compounds as described in WO 02/50027 or WO 04/007455.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in PCT/US 11833, PCT/US 11490, DE 10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with bile acid absorption inhibitor (see, for example, U.S. Pat. No. 6,245,744 or U.S. Pat. No. 6,221,897), such as, for example, HMR 1741.

In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512), such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein(a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]-phenyl]methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554–558), NPY antagonists, e.g. naphthalene-1-sulfonic acid {4-[(4-aminoquinazolin-2-ylamino)methyl]-cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-yl-urea hydrochloride (SB-334867-A)), cannabinoid 1 receptor antagonists (e.g. rimonabant or compounds as described in WO 02/28346), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed sertoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873–881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615–1622.

In one embodiment, the other active ingredient is dexamphatamine or amphetamine.

In one embodiment, the other active ingredient is a blood pressure reducing agent, such as, for example, an ACE inhibitor.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In one embodiment, the other active ingredient is rimonabant.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230–6. ) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

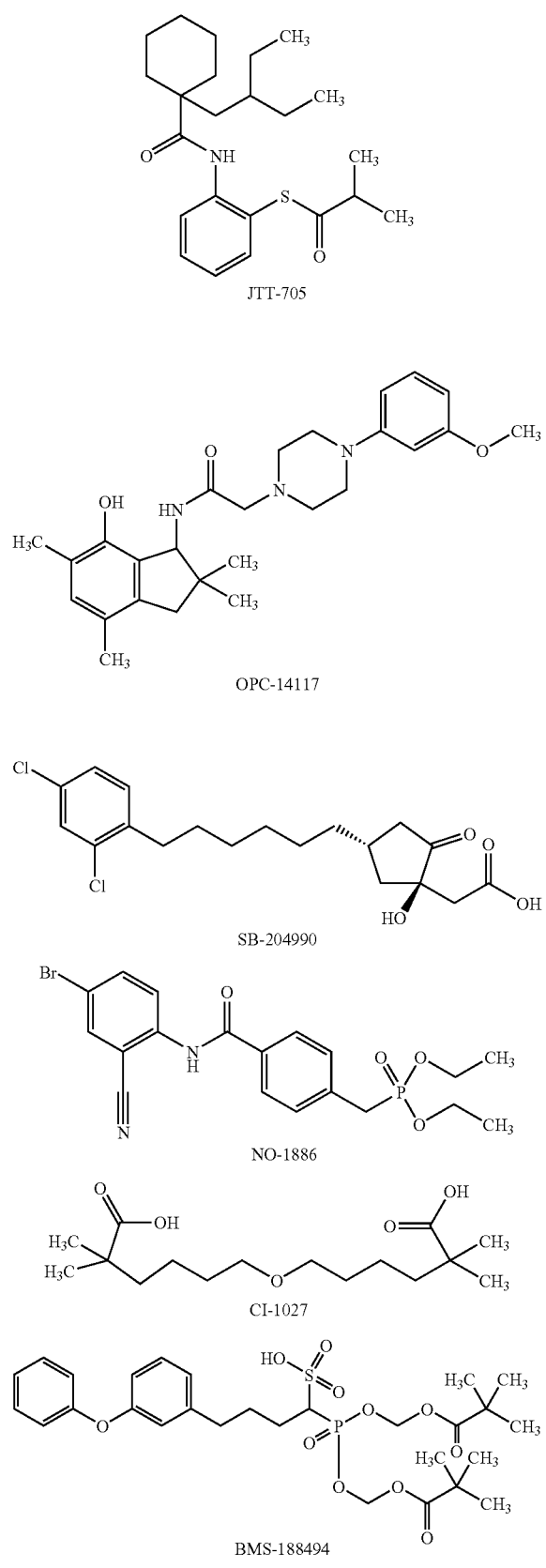

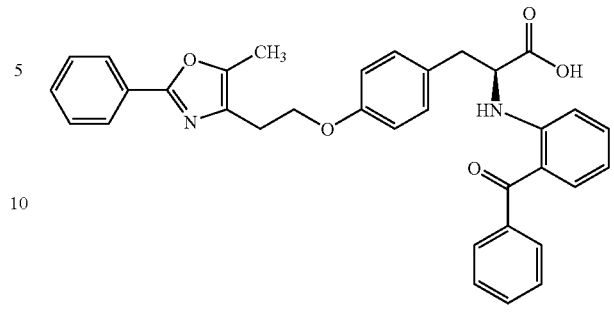

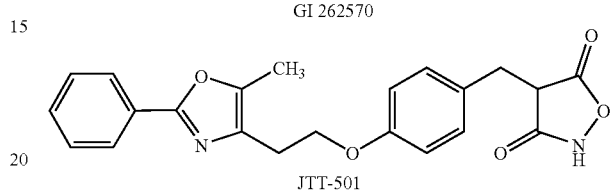

The theoretical examples detailed below in table I serve to illustrate the invention. They may be prepared in analogy to the exemplary embodiments.

TABLE I

I

| | R1 | R2 |
|---|---|---|
| a | H | Me |
| b | H | i-Pr |
| e | H | c-hexyl |
| f | Me | H |
| g | i-Pr | H |
| I | i-Pr | Me |
| j | 1-adamantyl | H |
| k | 1-hydroxyadamant-3-yl | H |
| l | Ph | H |
| m | 2-pyridyl | H |
| n | —(CH2)2—NH-2-pyridyl | H |
| o | 1,1-dimethyl-2-phenyl | H |
| p | 4-methylcyclohexyl-NH-C(O)-cyclohexyl | H |
| q | 4-methylpiperidin-1-yl-C(O)-cyclohexyl | H |
| r | Me | —CH2—CH(CH3)2 |
| t | —CH2—CH2—OH | —CH2—CH(CH3)2 |
| u | —CH2—CH2—OCH3 | —CH2—CH2-phenyl |
| v | —CH2—CH2—N(CH3)2 | —CH2—CH(CH3)2 |

TABLE I-continued

| | R1 | R2 |
|---|---|---|
| w | 2-pyridyl | Me |
| x | 2-thienyl | benzyl (CH2-Ph) |
| y | —CH2—CH(CH3)2 | —CH2—CH(CH3)2 |
| aa | c-pentyl | CH2—CH2—CH3 |
| ba | H | CH2—CH=C(CH3)2 |
| ca | H | CH3 |
| da | H | CH2—CH3 |
| ja | H | CH2—C(CH3)3 |
| la | H | C(CH3)3 |
| ma | H | CH(CH3)(Ph) |
| pa | H | CH2—CH2—CH(CH3)2 |
| sa | H | cyclohexylmethyl |
| ta | H | cyclopentyl |
| va | H | 4-methylcyclohexyl |
| wa | H | 4-(hydroxymethyl)cyclohexyl |
| xa | H | 4-hydroxycyclohexyl |
| ya | H | 4-methoxycyclohexyl |
| za | H | cyclohexyl |
| ab | H | cyclopentyl |
| bb | H | 4-aminocyclohexyl |

TABLE I-continued

| | R1 | R2 |
|---|---|---|
| eb | H | 4-(dimethylamino)cyclohexyl |
| gb | H | 1-methylpiperidin-4-yl |
| pb | H | 4-(SF5)phenyl |
| qb | H | 3,5-difluorophenyl |
| rb | H | 4-fluorophenyl |
| sb | H | 4-(trifluoromethyl)phenyl |
| tb | H | 4-phenoxyphenyl |
| ub | H | 2-thienyl |
| vb | H | 3-thienyl |
| wb | H | 2-oxazolyl |

TABLE I-continued

I

[Structure: pyrrolizine core with R1, R2 substituents on nitrogen-bearing carbon, ketone, and CN group]

| | R1 | R2 |
|---|---|---|
| zb | H | [ethyl-pyridin-3-yl group] |
| ac | H | [4-ethyl-piperidine-N-sulfonyl-phenyl group] |
| bc | H | [4-ethyl-cyclohexyl-NH-S(=O)2-methyl group] |
| cc | H | [4-methyl-piperidine-N-S(=O)2-methyl group] |

The compounds of the formula I are notable for beneficial effects on lipid and carbohydrate metabolism, in particular they lower the blood glucose level and are suitable for the treatment of type 2 diabetes, of insulin resistance, of dyslipidemias and of metabolic syndrome/syndrome X. The compounds are also suitable for the prophylaxis and treatment of arteriosclerotic manifestations. The compounds can be employed alone or in combination with other blood glucose-lowering active ingredients. The compounds act as DPP-IV inhibitors and are also suitable for the treatment of disorders of wellbeing and other psychiatric indications such as, for example, depressions, anxiety states, anxiety neuroses, schizophrenia and for the treatment of disorders associated with the circadian rhythm, for weight reduction in mammals, for the treatment of immunological disorders, and for the treatment of drug abuse. They are also suitable for the treatment of cancer, arthritis, osteoarthritis, osteoporosis, sleep disorders, sleep apnea, female and male sexual disorders, inflammations, acne, pigmentation of the skin, disorders of steroid metabolism, skin diseases, psoriasis, mycoses, neurodegenerative diseases, multiple sclerosis and Alzheimer's disease.

The activity of the compounds was assayed as follows:

Activity Assay

Measurement of the DPP-IV activity:

Material:
DPP-IV from porcine kidney (Sigma, Munich)
H-Ala-Pro-AFC (Bachem, Weil am Rhein)

Assay Conditions:
DPP-IV (1 mU/ml, final concentration)
H-Ala-Pro-AFC (15 µM, final concentration)
in Tris/HCl (40 mM, pH 7.4), total volume 0.2 ml The reaction was carried out at room temperature for various times (typically 10 min) and stopped at the end of the reaction by adding 20 µl of $ZnCl_2$ (1M). The H-Ala-Pro-AFC conversion was determined fluorometrically by measuring the emission at 535 nm after excitation at 405 nm. When inhibitors were added, the added buffer volume was adapted so that a total volume of 200 µl was maintained for the assay mixture.

IC50 values for inhibitors were determined by varying the inhibitor concentrations with the stated substrate concentration of 15 µM. Ki and Km values were found by appropriate variation of substrate concentration and inhibitor concentration as described (Dixon, M. and Webb, E. C.(1979) Enzymes, third edition, pp. 47–206, Academic Press). The values for Km, IC50 and Ki were calculated using a commercially available software package (Leatherbarrow, R. J. (1992) GraFit Version 3.0, Erithacus Software Ltd. Staines, U.K.).

The measurement yielded the following value:

| Example No. | IC-50 | Remarks |
|---|---|---|
| 1) | | |

Exemplary embodiment 1 was prepared as follows:

1) (3S,6R,7aS)-6-amino-5-oxo-hexahydro-pyrrolizine-3-carbonitrile trifluoroacetate 1a) tert-butyl (S)-5-oxopyrrolidine-2-carboxylate 129 g of L-pyroglutamic acid were suspended in 2 l of tert-butyl acetate. 30 ml of a 70% strength solution of perchloric acid in water were added thereto. The mixture was then stirred at room temperature for 12 h. It was cooled to 0° C. and the pH of the solution was adjusted to 7 by cautious addition of a 2N NaOH solution. The phases were separated and the organic phase was washed twice with 300 ml of a saturated sodium chloride solution each time. The organic phase was then dried with sodium sulfate. The solvents were removed in vacuo, and the residue was stirred with heptane. The solid obtained in this way was filtered off with suction. The mother liquor was concentrated in vacuo, and the solid obtained in this way was also filtered off with suction.

Yield: 157 g of tert-butyl (S)-5-oxopyrrolidine-2-carboxylate

MS: 186 (M+H)

1b) di-tert-butyl (S)-5-oxopyrrolidine-1,2-dicarboxylate 120 g of tert-butyl (S)-5-oxopyrrolidine-2-carboxylate were dissolved in 1.3 l of dichloromethane and cooled to 0° C. 3.9 g of 4-dimethylaminopryidine and 141 g of di-tert-butyl dicarbonate were added thereto. The mixture was stirred at 0° C. for 1 h and at room temperature for 12 h. The volume of the solution was then concentrated to about 300 ml in vacuo. The solution obtained in this way was filtered through 500 g of silica gel, eluting first with dichloromethane and then with 5% ethyl acetate in dichloromethane. The product fractions were combined and freed of solvents in vacuo.

Yield: 146 g of di-tert-butyl (S)-5-oxopyrrolidine-1,2-dicarboxylate

MS: 186 (M+H-Boc)

1c) di-tert-butyl (S)-5-hydroxypyrrolidine-1,2-dicarboxylate 93 g of di-tert-butyl (S)-5-oxopyrrolidine-1,2-dicarboxylate were dissolved in 600 ml of THF and cooled to −78° C. 392 ml of a 1N solution of lithium triethylborohydride in THF were added dropwise over the course of 90 min. The mixture was then stirred at −70° C. for 30 min. Subsequently, 240 ml of saturated sodium bicarbonate solution were added dropwise to the solution. The temperature was allowed to rise to −15° C. and then 160 ml of a 30% strength hydrogen peroxide solution were added dropwise. The mixture was then stirred at room temperature for 30 min. The phases were then separated, and the organic phase was concentrated in vacuo. The residue was taken up in 500 ml of tert-butyl methyl ether and washed 3 times with 300 ml of a 10% strength solution of sodium bicarbonate in water each time and twice with 300 ml of a saturated sodium chloride solution each time. The organic phase was dried with sodium sulfate, and the solvents were removed in vacuo. The crude product obtained in this way was employed without further purification in the next reaction.

Yield: 76 g of di-tert-butyl (S)-5-hydroxypyrrolidine-1,2-dicarboxylate

MS: 170 (M+H-Boc-H2O)

1d) di-tert-butyl (2S ,5S)-5-ethoxycarbonylmethylpyrrolidine-1,2-dicarboxylate 3,2 g of a 60% dispersion of sodium hydride in mineral oil were suspended in 300 ml of THF. 20.7 g of ethyl diethylphosphonoacetate in 50 ml of THF were added dropwise thereto. The mixture was stirred at room temperature for 2 h and was then cooled to −78° C. A solution of 19 g of di-tert-butyl (S)-5-hydroxypyrrolidine-1,2-dicarboxylate in 100 ml THF was then added dropwise, and the mixture was allowed to reach room temperature and was stirred for 24 h. The THF was removed in vacuo, and the residue was partitioned between 250 ml of water and 250 ml of dichloromethane. The organic phase was dried with sodium sulfate and concentrated in vacuo. The residue was chromatographed on silica gel. The product was obtained as an approx. 95:5 mixture of diastereomers (approx. 95% 5S, 5% R).

Yield: 16 g of di-tert-butyl (2S,5S)-5-ethoxycarbonylmethylpyrrolidine-1,2-dicarboxylate (contains about 5% di-tert-butyl (2S,5R)-5-ethoxycarbonylmethylpyrrolidine-1,2-dicarboxylate)

MS: 202 (M+H-Boc-tert-butyl)

1e) di-tert-butyl (2S,5S)-5-hydroxyethylpyrrolidine-1,2-dicarboxylate 43 g of the product from 1d were dissolved in 300 ml of diethyl ether. A solution of 3.1 g of lithium borohydride in 300 ml of diethyl ether was added dropwise thereto. The mixture was stirred for 6 h and the reaction was stopped by cautious addition of 300 ml of a saturated potassium bicarbonate solution. The phases were separated and the organic phase was washed with 250 ml of a saturated sodium chloride solution. The organic phase was dried with sodium sulfate, and the solvent was removed in vacuo. The residue was chromatographed on silica gel.

Yield 33 g of di-tert-butyl (2S,5S)-5-hydroxyethylpyrrolidine-1,2-dicarboxylate

MS: 204 (M+H-Boc-tert-butyl)

1f) di-tert-butyl (2S,5S)-5-(2-benzylamino-2-cyanoethyl)pyrrolidine-1,2-dicarboxylate 1.4 g of di-tert-butyl (2S,5S)-5-hydroxyethylpyrrolidine-1,2-dicarboxylate were dissolved in 10 ml of dichloromethane. A solution of 2.45 g of 1,1-dihydro-1,1,1-triacetoxy-1,2-benzodoxol-3(1H)-one (Dess-Martin periodinan) in 25 ml of dichloromethane was added dropwise thereto. The mixture was stirred for 30 min and then diluted with 200 ml of tert-butyl methyl ether. It was washed once with 150 ml of a 10% strength sodium bicarbonate solution, once with 150 ml of a 5% strength sodium thiosulfate solution and once with 150 ml of a saturated sodium chloride solution. The organic phase was dried with sodium sulfate, and the solvents were removed in vacuo. The crude product obtained in this way was dissolved in 20 ml of THF. 535 mg of benzylamine were added thereto, and the mixture was stirred for 1 h. Then 0.66 ml of trimethylsilyl cyanide and 110 mg of indium(III) chloride were successively added. The mixture was stirred at room temperature for 14 h. After filtration through kieselguhr, the solvents were removed in vacuo, and the residue was chromatographed on silica gel.

Yield: 1.15 g of di-tert-butyl (2S,5S)-5-(2-benzylamino-2-cyanoethyl)pyrrolidine-1,2-dicarboxylate

MS: 430 (M+H)

1g) di-tert-butyl (2S,5S)-5-(2-benzylamino-2-carbamoylethyl)pyrrolidine-1,2-dicarboxylate 2.6 g of di-tert-butyl (2S,5S)-5-(2-benzylamino-2-cyanoethyl)pyrrolidine-1,2-dicarboxylate were dissolved in 6.5 ml of dimethyl sulfoxide. 373 mg of finely ground potassium carbonate and 1.08 ml of a 30% strength hydrogen peroxide solution were added thereto. The mixture was stirred at room temperature for 14 h and was then heated at 35° C. for 30 min. The solution was diluted with 60 ml of water and extracted 3 times with 100 ml of ethyl acetate each time. The combined organic phases were washed once with 120 ml of a saturated sodium chloride solution and dried with sodium sulfate. The solvents were removed in vacuo, and the residue was chromatographed on silica gel.

Yield: 2.4 g of di-tert-butyl (2S,5S)-5-(2-benzylamino-2-carbamoylethyl)pyrrolidine-1,2-dicarboxylate

MS: 448 (M+H)

1h) (2S,5S)-5-(2-benzylamino-2-carboxyethyl)pyrrolidine-1,2-dicarboxylic acid 1-tert-butyl ester 2.2 g of di-tert-butyl (2S,5S)-5-(2-benzylamino-2-carbamoylethyl)pyrrolidine-1,2-dicarboxylate were dissolved in 20 ml of ethanol and 5 ml of water. 1.2 g of solid sodium hydroxide were added thereto. The solution was then boiled under reflux for 36 h. For workup, it was cooled to room temperature and neutralized with acetic acid, and the ethanol was removed in vacuo. The residue was diluted with 20 ml of water and adjusted to a pH of 3 with acetic acid. The mixture was extracted 3 times with 30 ml of 5:1 ethyl acetate/butanol each time. The organic phases were combined and concentrated in vacuo. The residue was chromatographed on silica gel.

Yield:
1700 mg of (2S,5S)-5-(2-benzylamino-2-carboxyethyl)pyrrolidine-1,2-dicarboxylic acid 1-tert-butyl ester

MS: 393 (M+H)

1i) (2S,5S)-5-(2-amino-2-carboxyethyl)pyrrolidine-1,2-dicarboxylic acid 1-tert-butyl ester hydrogen acetate 1600 mg of (2S,5S)-5-(2-benzylamino-2-carboxyethyl) pyrrolidine-1,2-dicarboxylic acid 1-tert-butyl ester were dissolved in 30 ml of acetic acid. 100 mg of 20% palladium hydroxide on activated carbon were added thereto, and the mixture was hydrogenated under an atmosphere of 1 bar of hydrogen for 1 h. Ar was then passed over the solution for 10 min. The catalyst was filtered off through kieselguhr and the filter cake was washed with 20 ml of acetic acid. The combined organic phases were concentrated in vacuo. The crude product was employed without further purification in the next reaction.

Yield: 1500 mg of (2S,5S)-5-(2-amino-2-carboxyethyl) pyrrolidine-1,2-dicarboxylic acid 1-tert-butyl ester hydrogen acetate

MS: 303 (M+H)

1j) (2S,5S)-5-(2-benzyloxycarbonylamino-2-carboxyethyl) pyrrolidine-1,2-dicarboxylic acid 1-tert-butyl ester 1450 mg of (2S,5S)-5-(2-amino-2-carboxyethyl)pyrrolidine-1,2-dicarboxylic acid 1-tert-butyl ester hydrogen acet dissolved in 30 ml of water and 40 ml of dioxane. Then 1600 mg of potassium bicarbonate and 997 mg of N-(benzyloxycarbonyloxy)succinimide were successively added. The mixture was stirred at room temperature for 4 h and then the dioxane was removed in vacuo. The residue was diluted with 20 ml of water, and the pH was adjusted to 2 with 1N HCl solution. The aqueous phase was extracted 4 times with 60 ml of ethyl acetate each time. The combined organic phases were dried with sodium sulfate and concentrated in vacuo.

Yield: 1570 mg of (2S,5S)-5-(2-benzyloxycarbonylamino-2-carboxyethyl)pyrrolidine-1,2-dicarboxylic acid 1-tert-butyl ester MS: 337 (M+H-Boc)

1k) 1-tert-butyl 2-methyl (2S,5S)-5-(2-benzyloxycarbonylamino-2-methoxycarbonyl-ethyl)pyrrolidine-1,2-dicarboxylate 1450 mg of (2S,5S)-5-(2-benzyloxycarbonylamino-2-carboxyethyl)pyrrolidine-1,2-dicarboxylic acid 1-tert-butyl ester were dissolved in 15 ml of THF and 5 ml of methanol. The solution was cooled to 0° C., and 4 ml of a 2M solution of trimethylsilyldiazomethane in hexane were added. The mixture was allowed to reach room temperature over the course of 1 h and then the reaction was stopped by cautious addition of acetic acid. After stirring for 10 min, the solvents were removed in vacuo. The residue was purified by chromatography on silica gel.

Yield: 1500 mg of 1-tert-butyl 2-methyl (2S,5S)-5-(2-benzyloxycarbonylamino-2-methoxycarbonylethyl)pyrrolidine-1,2-dicarboxylate MS: 365 (M+H-Boc)

1l) methyl (3S,7aS)-6-benzyloxycarbonylamino-5-oxohexahydropyrrolizine-3-carboxylate 1500 mg of 1-tert-butyl 2-methyl (2S,5S)-5-(2-benzyloxycarbonylamino-2-methoxycarbonylethyl)pyrrolidine-1,2-dicarboxylate were mixed with 0.2 ml of thioanisole. Then 10 ml of trifluoroacetic acid were added, and the mixture was stirred for 45 min. The solvents were then removed in vacuo, and the residue was taken up in 10 ml of pyridine. 1.1 ml of diisopropylethylamine were added, and the mixture was heated at 95° C. for 3 h. The solvents were removed in vacuo, and the residue was chromatographed on silica gel.

Yield: 540 mg of methyl (3S,7aS)-6-benzyloxycarbonylamino-5-oxohexahydropyrrolizine-3-carboxylate

MS: 333 (M+H)

1l) methyl (3S,7aS)-6-tert-butoxycarbonylamino-5-oxohexahydropyrrolizine-3-carboxylate 540 mg of methyl (3S,7aS)-6-benzyloxycarbonylamino-5-oxohexahydropyrrolizine-3-carboxylate were dissolved in 10 ml of glacial acetic acid. 50 mg of 10% palladium on activated carbon were added, and the mixture was hydrogenated under an atmosphere of is 1 bar of hydrogen for 1 h. Ar was then passed over the solution for 10 min, and it was then filtered through a membrane filter. The solvent was removed in vacuo, and the residue was taken up in 30 ml of acetonitrile. 350 mg of di-tert-butyl dicarbonate and 0.28 ml of diisopropylethylamine were successively added, and the mixture was stirred at room temperature for 1 h. The solvents were removed in vacuo, and the residue was purified by chromatography on silica gel.

Yield: 440 mg of methyl (3S,7aS)-6-tert-butoxycarbonylamino-5-oxohexahydropyrrolizine-3-carboxylate MS: 243 (M+H-tBu)

1m) tert-butyl ((2R,5S,7aS)-5-carbamoyl-3-oxohexahydropyrrolizin-2-yl)carbamate and tert-butyl ((2S,5S,7aS)-5-carbamoyl-3-oxohexahydropyrrolizin-2-yl)-carbamate 100 ml of a 7M solution of ammonia in methanol were added to 465 mg of methyl (3S,7aS)-6-tert-butoxycarbonylamino-5-oxohexahydropyrrolizine-3-carboxylate at 0° C. The mixture was allowed slowly to reach room temperature and was stirred for 14 h. The solvents were then removed in vacuo. The residue was chromatographed on silica gel.

Yield: 200 mg of tert-butyl ((2R,5S,7aS)-5-carbamoyl-3-oxohexahydropyrrolizin-2-yl)-carbamate MS: 228 (M+H-tBu)

and 170 mg of tert-butyl ((2S,5S,7aS)-5-carbamoyl-3-oxohexahydropyrrolizin-2-yl)-carbamate MS: 228 (M+H-tBu)

1n) tert-butyl ((2R,5S,7aS)-5-cyano-3-oxohexahydropyrrolizin-2-yl)carbamate 100 mg of tert-butyl ((2R,5S,7aS)-5-carbamoyl-3-oxohexahydropyrrolizin-2-yl)carbamate were dissolved in 2 ml of dimethylformamide, and 65 mg of cyanuric chloride were added. The mixture was stirred for 3 h, and the dimethylformamide was removed in vacuo. The residue was chromatographed on silica gel.

Yield: 85 mg of tert-butyl ((2R,5S,7aS)-5-cyano-3-oxohexahydropyrrolizin-2-yl)carbamate MS: 210 (M+H-tBu)

1o) (3S,6R,7aS)-6-amino-5-oxohexahydropyrrolizine-3-carbonitrile trifluoroacetate 80 mg of tert-butyl ((2R,5S,7aS)-5-cyano-3-oxohexahydropyrrolizin-2-yl)carbamate were C reacted with 10% thioanisole in 1 ml of trifluoroacetic acid for 30 min. The solvents were then removed in vacuo, and the residue was stirred with diusopropyl ether.

Yield: 73 mg of (3S,6R,7aS)-6-amino-5-oxohexahydropyrrolizine-3-carbonitrile trifluoroacetate

MS: 166 (M+H)

The invention claimed is:

1. A compound of the formula I,

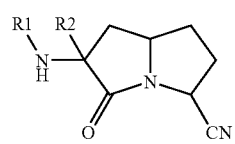

wherein
R1 is H, $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, heterocyclyl, COR3, COOR3, CONR3R4 or CN,
  wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, SH, $SF_5$, OH, $(C_1-C_6)$-alkyl, —$CF_3$, $(C_2-C_6)$-alkenyl, $(C_2-C_6)$-alkynyl, OR3, OP(O)(OR3)$_2$, NR3R4, NR3CONR3R4, COR3, OCOR3, OCOOR3, COOR3, CONR3R4, OCONR3R4, $(C_1-C_6)$-alkylene-OR3, $(C_1-C_6)$-alkylene-NR3R4, $(C_1-C_6)$-alkylene-NR3SO$_2$R4, $(C_1-C_6)$-alkylene-SR3, alkylene-S(O)R3, alkylene-S(O)$_2$R3, alkylene-S(O)$_2$NR3R4, $(C_1-C_6)$-alkylene-COR3, $(C_1-C_6)$-alkylene-COOR3, $(C_1-C_6)$-alkylene-CONR3R4, SR3, SOR3, SO$_2$R3, SO$_2$NR3R4, NR3SO$_2$R4, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl;
R2 is H, $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, heterocyclyl, COR3, COOR3, CONR3R4 or CN,
  wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, SH, $SF_5$, OH, $(C_1-C_6)$-alkyl, —$CF_3$, $(C_2-C_6)$-alkenyl, $(C_2-C_6)$-alkynyl, OR3, OP(O)(OR3)$_2$, NR3R4, NR3CONR3R4, COR3, OCOR3, OCOOR3, COOR3, CONR3R4, OCONR3R4, $(C_1-C_6)$-alkylene-OR3, $(C_1-C_6)$-alkylene-NR3R4, $(C_1-C_6)$-alkylene-NR3SO$_2$R4, $(C_1-C_6)$-alkylene-SR3, alkylene-S(O)R3, alkylene-S(O)$_2$R3, alkylene-S(O)$_2$NR3R4, $(C_1-C_6)$-alkylene-COR3, $(C_1-C_6)$-alkylene-COOR3, $(C_1-C_6)$-alkylene-CONR3R4, SR3, SOR3, SO$_2$R3, SO$_2$NR3R4, NR3SO$_2$R4, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl;
R3, R4 are each, independently of one another, H, $(C_1-C_6)$-alkyl, —$CF_3$, $(C_3-C_{10})$-cycloalkyl, $(C_6-C_{10})$-aryl, heterocyclyl, $(C_1-C_6)$-alkylene-CONR5R6, CONR5R6, $(C_1-C_6)$-alkylene-COOR5, COOR5, COR5, $(C_1-C_6)$-alkylene-COR5, $(C_1-C_6)$-alkylene-OR5, $(C_1-C_6)$-alkylene-NR5R6, $(C_1-C_6)$-alkylene-SR5, $(C_1-C_6)$-alkylene-S(O)R5, $(C_1-C_6)$-alkylene-S(O)$_2$R5, S(O)R5, S(O)$_2$R5, $(C_1-C_4)$-alkylene-$(C_6-C_{10})$-aryl or $(C_1-C_4)$-alkylene-heterocyclyl;
R5, R6 are each, independently of one another, H, $(C_1-C_6)$-alkyl, $(C_1-C_6)$-alkylene-$(C_6-C_{10})$-aryl, —$(C_6-C_{10})$-aryl, heterocyclyl or $(C_1-C_6)$-alkylene-heterocyclyl;
and pharmaceutically acceptable salts thereof.

2. The compound of claim 1 wherein
R1 is H;
R2 is H, $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, heterocyclyl, COR3, COOR3, CONR3R4 or CN,
  wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, SH, $SF_5$, OH, $(C_1-C_6)$-alkyl, —$CF_3$, $(C_2-C_6)$-alkenyl, $(C_2-C_6)$-alkynyl, OR3, OP(O)(OR3)$_2$, NR3R4, NR3CONR3R4, COR3, OCOR3, OCOOR3, COOR3, CONR3R4, OCONR3R4, $(C_1-C_6)$-alkylene-OR3, $(C_1-C_6)$-alkylene-NR3R4, $(C_1-C_6)$-alkylene-NR3SO$_2$R4, $(C_1-C_6)$-alkylene-SR3, alkylene-S(O)R3, alkylene-S(O)$_2$R3, alkylene-S(O)$_2$NR3R4, $(C_1-C_6)$-alkylene-COR3, $(C_1-C_6)$-alkylene-COOR3, $(C_1-C_6)$-alkylene-CONR3R4, SR3, SOR3, SO$_2$R3, SO$_2$NR3R4, NR3SO$_2$R4, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl;
R3, R4 are each, independently of one another, H, $(C_1-C_6)$-alkyl, —$CF_3$, $(C_3-C_{10})$-cycloalkyl, $(C_6-C_{10})$-aryl, heterocyclyl, $(C_1-C_6)$-alkylene-CONR5R6, CONR5R6, $(C_1-C_6)$-alkylene-COOR5, COOR5, COR5, $(C_1-C_6)$-alkylene-COR5, $(C_1-C_6)$-alkylene-OR5, $(C_1-C_6)$-alkylene-NR5R6, $(C_1-C_6)$-alkylene-SR5, $(C_1-C_6)$-alkylene-S(O)R5, $(C_1-C_6)$-alkylene-S(O)$_2$R5, S(O)R5, S(O)$_2$R5, $(C_1-C_4)$-alkylene-$(C_6-C_{10})$-aryl or $(C_1-C_4)$-alkylene-heterocyclyl;
R5, R6 are each, independently of one another, H, $(C_1-C_6)$-alkyl, $(C_1-C_6)$-alkylene-$(C_6-C_{10})$-aryl, —$(C_6-C_{10})$-aryl, heterocyclyl or $(C_1-C_6)$-alkylene-heterocyclyl;
and pharmaceutically acceptable salts thereof.

3. The compound of claim 2 wherein:
R1 is H;
R2 is $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, heterocyclyl, COR3, COOR3, CONR3R4 or CN,
  wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, SH, $SF_5$, OH, $(C_1-C_6)$-alkyl, —$CF_3$, $(C_2-C_6)$-alkenyl, $(C_2-C_6)$-alkynyl, OR3, OP(O)(OR3)$_2$, NR3R4, NR3CONR3R4, COR3, OCOR3, OCOOR3, COOR3, CONR3R4, OCONR3R4, $(C_1-C_6)$-alkylene-OR3, $(C_1-C_6)$-alkylene-NR3R4, $(C_1-C_6)$-alkylene-NR3SO$_2$R4, $(C_1-C_6)$-alkylene-SR3, alkylene-S(O)R3, alkylene-S(O)$_2$R3, alkylene-S(O)$_2$NR3R4, $(C_1-C_6)$-alkylene-COR3, $(C_1-C_6)$-alkylene-COOR3, $(C_1-C_6)$-alkylene-CONR3R4, SR3, SOR3, SO$_2$R3, SO$_2$NR3R4, NR3SO$_2$R4, $(C_1-C_6)$-alkylene-$(C_3-C_{10})$-Cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl;
R3, R4 are each, independently of one another, H, $(C_1-C_6)$-alkyl, —$CF_3$, $(C_3-C_{10})$-cycloalkyl, $(C_6-C_{10})$-aryl, heterocyclyl, $(C_1-C_6)$-alkylene-CONR5R6, CONR5R6, $(C_1-C_6)$-alkylene-COOR5, COOR5, COR5, $(C_1-C_6)$-alkylene-COR5, $(C_1-C_6)$-alkylene-OR5, $(C_1-C_6)$-alkylene-NR5R6, $(C_1-C_6)$-alkylene-SR5, $(C_1-C_6)$-alkylene-S(O)R5, $(C_1-C_6)$-alkylene-S(O)$_2$R5, S(O)R5, S(O)$_2$R5, $(C_1-C_4)$-alkylene-$(C_6-C_{10})$-aryl or $(C_1-C_4)$-alkylene-heterocyclyl;
R5, R6 are each, independently of one another, H, $(C_1-C_6)$-alkyl, $(C_1-C_6)$-alkylene-$(C_6-C_{10})$-aryl, —$(C_6-C_{10})$-aryl, heterocyclyl or $(C_1-C_6)$-alkylene-heterocyclyl;
and pharmaceutically acceptable salts thereof.

4. The compound of claim 3 wherein:
R1 is H;
R2 is $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, a pyrrolidino, piperidino, hexamethyleneimino, morpholino, piperazino, thiomorpholino or homopiperazino radical, wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, a pyrrolidino, piperidino, hexamethyleneimino, morpholino, piperazino, thiomorpholino and homopiperazino radicals are optionally substituted one or more times by F, Cl, Br, CN, $SF_5$, OH, $(C_1-C_6)$-alkyl, —$CF_3$, $(C_2-C_6)$-alkenyl, OR3, NR3R4, NR3CONR3R4, COR3, OCOR3, $CO_2$R3, CONR3R4, OCONR3R4, $(C_1-C_6)$-alkylene-OR3, $(C_1-C_6)$-alkylene-NR3R4, $(C_1-C_6)$-alkylene-NR3$SO_2$R4, $(C_1-C_6)$-alkylene-SR3, alkylene-S(O)R3, alkylene-S(O)$_2$R3, alkylene-S(O)$_2$NR3R4, $(C_1-C_6)$-alkylene-COR3, $(C_1-C_6)$-alkylene-$CO_2$R3, $(C_1-C_6)$-alkylene-CONR3R4, SR3, SOR3, $SO_2$R3, $SO_2$NR3R4, NR3$SO_2$R4, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl, wherein said $(C_6-C_{10})$-aryl is optionally substituted one or more times by F, Cl, Br, I, CN, OH, —$CF_3$, $(C_1-C_6)$-alkyl, OR3, NR3R4, COR3, CO2R3 or CONR3R4, and wherein said heterocyclyl is optionally substituted one or more times by F, Cl, Br, CN, $NO_2$, OH, —$CF_3$, $(C_1-C_6)$-alkyl, OR3, NR3R4, COR3, CO2R3 or CONR3R4;

R3, R4 are each, independently of one another, H, $(C_1-C_6)$-alkyl, —$CF_3$, $(C_3-C_{10})$-cycloalkyl, $(C_6-C_{10})$-aryl, heterocyclyl, $(C_1-C_6)$-alkylene-CONR5R6, $(C_1-C_6)$-alkylene-COOR5, $(C_1-C_6)$-alkylene-COR5, $(C_1-C_6)$-alkylene-OR5, $(C_1-C_6)$-alkylene-NR5R6, $(C_1-C_6)$-alkylene-SR5, $(C_1-C_6)$-alkylene-S(O)R5, $(C_1-C_6)$-alkylene-S(O)$_2$R5, $(C_1-C_4)$-alkylene-$(C_6-C_{10})$-aryl or $(C_1-C_4)$-alkylene-heterocyclyl;

R5, R6 are each, independently of one another, H, $(C_1-C_6)$-alkyl, $(C_3-C_{10})$-cycloalkyl, $(C_1-C_6)$-alkylene-$(C_6-C_{10})$-aryl, —$(C_6-C_{10})$-aryl, heterocyclyl or $(C_1-C_6)$-alkylene-$(C_3-C_{10})$-heterocyclyl;

and pharmaceutically acceptable salts thereof.

5. The compound of claim 4 wherein:

R1 is H;

R2 is $(C_1-C_{10})$-alkyl, $(C_3-C_{10})$-cycloalkyl, phenyl, $(C_1-C_6)$-alkylene-phenyl, a pyrrolidino, piperidino, hexamethyleneimino, morpholino, piperazino, thiomorpholino or homopiperazino radical;

and pharmaceutically acceptable salts thereof.

6. A pharmaceutical composition comprising one or more compounds of claim 1 and a pharmaceutically acceptable carrier.

7. The pharmaceutical composition of claim 6 further comprising at least one other active ingredient.

8. A method of reducing blood sugar comprising administering to a patient in need thereof a therapeutically effective amount of a compound of claim 1.

9. A method of treating type 2 diabetes comprising administering to a patient in need thereof a therapeutically effective amount of a compound of claim 1.

10. A method of treating insulin resistance comprising administering to a patient in need thereof a therapeutically effective amount of a compound of claim 1.

* * * * *